(12) United States Patent
Adajar

(10) Patent No.: US 10,758,273 B2
(45) Date of Patent: Sep. 1, 2020

(54) UTERINE MANIPULATOR DEVICE WITH CUTTING ELEMENT

(71) Applicant: Allan A. Adajar, Glenview, IL (US)

(72) Inventor: Allan A. Adajar, Glenview, IL (US)

( * ) Notice: Subject to any disclaimer, the term of this patent is extended or adjusted under 35 U.S.C. 154(b) by 754 days.

(21) Appl. No.: 15/369,860

(22) Filed: Dec. 5, 2016

(65) Prior Publication Data
US 2017/0156756 A1    Jun. 8, 2017

Related U.S. Application Data
(60) Provisional application No. 62/262,995, filed on Dec. 4, 2015.

(51) Int. Cl.
| | | |
|---|---|---|
| *A61B 17/42* | (2006.01) | |
| *A61B 17/3209* | (2006.01) | |
| *A61B 18/08* | (2006.01) | |
| *A61B 18/10* | (2006.01) | |
| *A61B 18/00* | (2006.01) | |
| *A61B 90/30* | (2016.01) | |
| *A61B 17/34* | (2006.01) | |

(52) U.S. Cl.
CPC ...... *A61B 17/4241* (2013.01); *A61B 17/3209* (2013.01); *A61B 18/082* (2013.01); *A61B 18/10* (2013.01); *A61B 17/3474* (2013.01); *A61B 2017/4225* (2013.01); *A61B 2018/00559* (2013.01); *A61B 2018/00595* (2013.01); *A61B 2090/306* (2016.02); *A61B 2090/309* (2016.02); *A61B 2218/006* (2013.01)

(58) Field of Classification Search
CPC ........................................... A61B 2018/00559
See application file for complete search history.

(56) References Cited

U.S. PATENT DOCUMENTS

| | | | | |
|---|---|---|---|---|
| 5,403,310 | A * | 4/1995 | Fischer | A61B 18/14 606/45 |
| 6,309,388 | B1 * | 10/2001 | Fowler | A61B 18/1485 600/564 |
| 6,641,581 | B2 * | 11/2003 | Muzzammel | A61B 18/14 606/41 |
| 6,730,085 | B2 * | 5/2004 | George | A61B 18/1485 600/564 |
| 6,994,677 | B1 * | 2/2006 | Buehlmann | A61B 18/148 600/567 |
| 8,608,738 | B2 * | 12/2013 | Brecheen | A61B 17/42 606/45 |
| 9,629,660 | B2 | 4/2017 | Einarsson | |
| 2002/0147448 | A1 * | 10/2002 | Fodor | A61B 18/14 606/48 |
| 2009/0318914 | A1 * | 12/2009 | Utley | A61B 18/1206 606/33 |
| 2017/0189065 | A1 | 6/2017 | Einarsson | |

* cited by examiner

*Primary Examiner* — Ronald Hupczey, Jr.
(74) *Attorney, Agent, or Firm* — Richards Patent Law P.C.

(57) ABSTRACT

A uterine manipulator device includes a shaft including a proximal end and a distal end, a cervical cup positioned on the shaft near the distal end, and a cutting tool. The cervical cup includes a first base and an annular wall with a rim. The cutting tool positioned along the rim of the cervical cup is rotatably coupled to the rim.

7 Claims, 7 Drawing Sheets

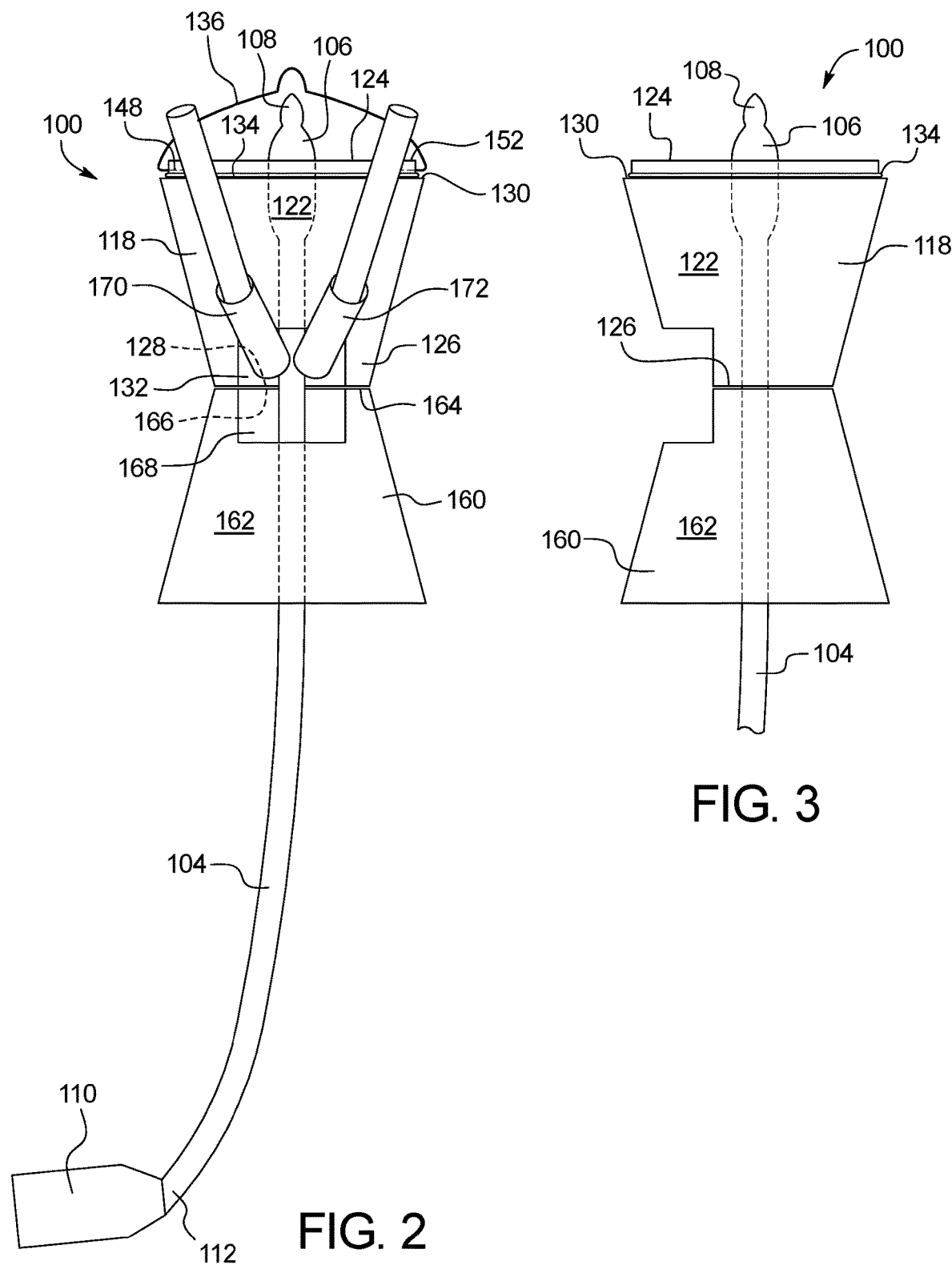

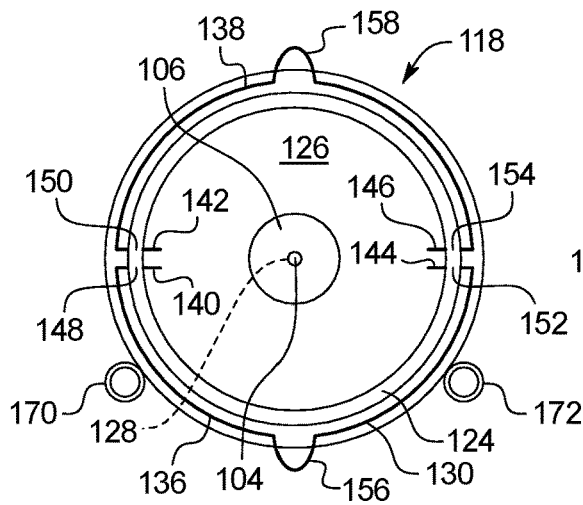
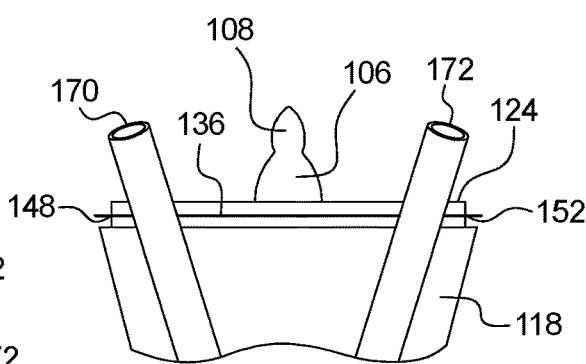
FIG. 5A · FIG. 6A
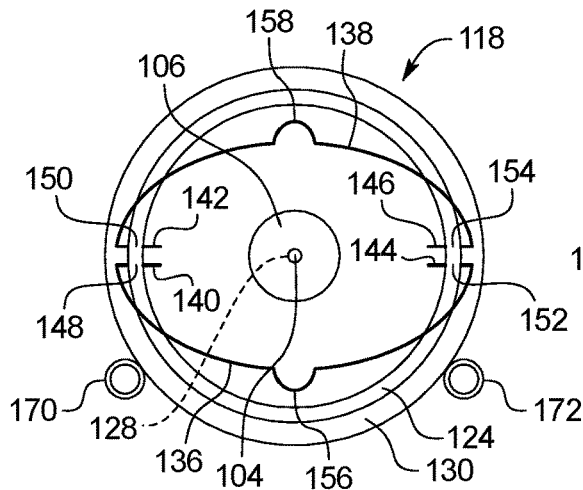
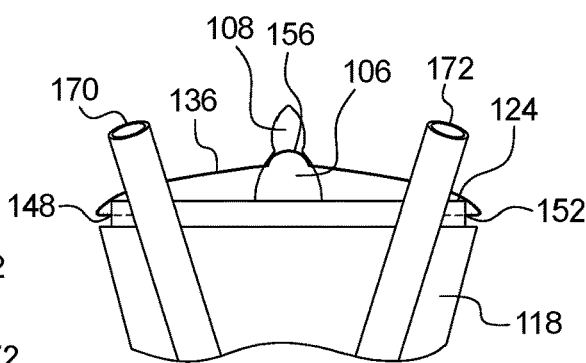
FIG. 5B · FIG. 6B
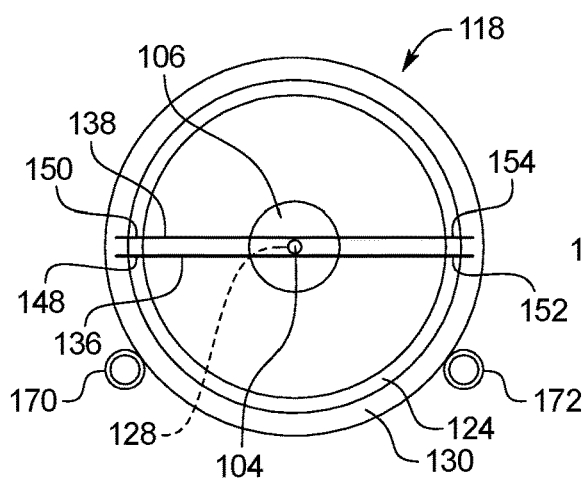
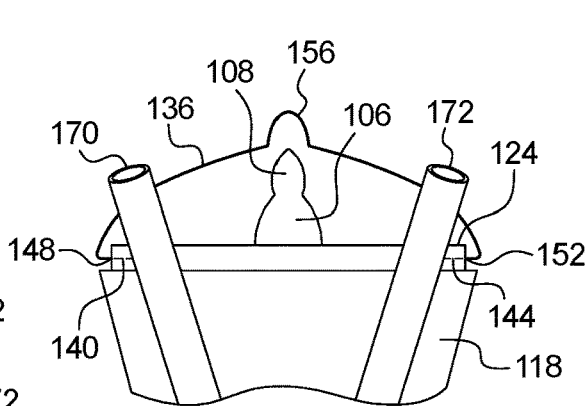
FIG. 5C · FIG. 6C

UTERINE MANIPULATOR DEVICE WITH CUTTING ELEMENT

CROSS-REFERENCE TO RELATED APPLICATIONS

This application incorporates by reference and claims the benefit of priority to U.S. Provisional Application No. 62/262,995 filed on Dec. 4, 2015.

BACKGROUND OF THE INVENTION

The present invention relates to a device for manipulating the uterus that delivers and removes gas from the patient's abdominal cavity during a laparoscopic surgical procedure. More specifically, the present invention relates to a device that efficiently transects the walls of the vagina while cycling gas through the cavity during a laparoscopic surgical procedure.

During a hysterectomy, a patient's uterus and cervix are surgically removed from the body. Utilization of the vaginal canal for abdominal access to reproductive organs is conventional in gynecologic surgery to minimize or eliminate the need to make incisions in the patient's skin. The use of laparoscopic or "minimally invasive" surgical procedures is becoming more common because of the reduced pain experienced by the patient, the reduced opportunity for infection, and faster recovery time as compared to the traditional open abdominal procedures.

In a laparoscopic hysterectomy, A camera and surgical tools are inserted through small incisions formed in the abdominal area to access the uterus within the abdominal cavity. The surgeon inserts a uterine manipulator through the vaginal canal to access the cervix. The surgeon may cut the vaginal tissue adjacent to the cervix using a laparoscopic cutting tool and a uterine manipulator, then remove the uterus and cervix through the vaginal canal.

Laparoscopic procedures routinely involve the insufflation of the abdominal cavity with pressurized gas in order for the camera to visualize the operative field. Gas such as carbon dioxide is used to distend the abdominal cavity. In procedures involving the cauterization of tissue, smoke created by the cauterization may hinder the surgeon's view of the operative field. Adequate visualization of the operative field requires cycling of the gas to remove the smoke. Two cannulas or lumens are inserted to simultaneously inject and remove gas to and from the abdominal cavity.

As minimally invasive surgery develops, there is also a trend in minimizing the size of the incision as well as the instrumentation. Small diameter cannulas placed through the abdominal wall incisions allow access and exchange of laparoscopic instruments. These cannulas also provide a means for gas exchange within the abdominal cavity. However, decreasing the diameters of the cannulas used to cycle gas while distending the abdominal cavity is limited by the requirement for adequate air flow, as the air flow rate is directly proportional to the cannula diameter.

A uterine manipulator is a surgical instrument that the surgeon uses to properly and effectively position the uterus within the pelvis and the abdominal cavity during medical procedures. A conventional uterine manipulator includes a balloon on a distal end of a shaft that is inserted into the uterus, such as the uterine manipulator device of U.S. Pat. No. 8,545,513, incorporated herein by reference. Grasping the handle on the proximal end of the shaft, the surgeon inserts a deflated balloon into the uterus, and then fills the balloon with water or other fluid. With the balloon expanded against the walls of the uterus, the surgeon can move and position the uterus by manipulating the shaft of the uterine manipulator. Movement of the uterus allows the surgeon to view anatomy around the uterus such as the posterior and anterior cul-de-sacs, the uterosacral and round ligaments, the fallopian tubes and ovaries, the cervix, and the bladder.

The uterine manipulator also includes a cervical engagement cup positioned on the shaft adjacent to the distal end. The cervical engagement cup aids in delineating anatomical structure as well as protecting vital structures such as the ureter and the uterine vessels. With the balloon positioned within the uterus, the cervical engagement cup receives the patient's cervix.

During a hysterectomy procedure, the surgeon inserts a cutting tool laparoscopically to cut along the rim of the cervical engagement cup. The small area to be cut at the junction of the cervix and the vaginal canal requires much precision in manipulation of the cutting tool. The surgeon controls the positioning of the cutting element of the cutting tool at the cervix-vaginal junction at a relatively large distance from outside of the body, either at the abdomen or the vagina. Manipulating the cutting element from outside of the body compounded by the high degree of precision required is difficult by even the most experienced surgeon's standards.

Further, light sources incorporated into surgical tools such as light delivery catheters and endoscopes are frequently introduced into the body to transilluminate anatomy. A transilluminating catheter delivers light to a distal portion of the body for performing phototherapeutic procedures as well as transillumination. Light emitting vaginal probes may be used to demarcate the vagina from the cervix. Various types of light emitting stents have been developed to transilluminate the ureters and uterine vessels from surrounding anatomy to prevent ureteral injury. However, such devices cannot transilluminate the upper vagina to identify the location of the ureters and its proximity to the uterine vessels while providing insufflation and smoke evacuation.

Consistent with the trend to minimize the size of laparoscopic incisions as well as the size and number of instrumentation, there is a need for a uterine manipulator device that provides multiple functionality during surgical procedures.

SUMMARY OF THE INVENTION

The present invention solves the above-mentioned problems by provide a uterine manipulator device that includes a cutting tool for cauterizing tissue as well as a light source for transilluminating the patient's cervix, upper vagina, ureters, and uterine vessels.

The uterine manipulator device includes a rigid shaft with a balloon positioned at a distal end. A cervical cup positioned on the shaft adjacent the distal end that receives the cervix during use includes an annular wall having a frustoconical shape with a rim extends from a base. The shaft protrudes through an opening within the base so that the balloon may be positioned within the annular wall of the cervical cup. The cervical cup includes an outwardly protruding ledge on the outer surface of the wall slightly spaced from the rim.

The cervical cup may include a light source to illuminate the surgeon's operative field. The light source may comprise a fiber optic or a plurality of light emitting diodes that are secured to the rim of the cervical cup. During a surgical procedure, the operative field is viewed through a camera within the abdominal cavity. The light source on the uterine manipulator device transilluminates the cervix so that the surgeon can determine where the cervical cup is located. The transillumination also allows the surgeon to identify pelvic anatomy such as the uterine arteries and the ureter.

First and second cauterizing heated elements or wires, or other cutting tools, are rotatably connected to the rim of the cervical cup. Each wire includes a notch to be grasped by a surgical tool during a procedure. The ends of the first and second wires are positioned next to one another so that the wires extend along the perimeter of the rim in an inactive position. Each of the first and second wires pivots approximately 90 degrees about the respective connection points to provide a full 180-degree rotation. In other embodiments, the uterine manipulator device may include a single wire that pivots approximately 180 degrees about opposing connection points. Still further, other embodiments may include any number of wires as desired. Once the device has been positioned and the patient's cervix is in the cervical cup, the wires are energized to cauterize tissue at the cervical/vaginal junction, thereby detaching the uterus from the vagina.

The first and second wires are energized by a current from a power source. In one embodiment, the uterine manipulator device includes a power source, such as a battery, within the handle. In other embodiments, the wires may be activated by a power source on a surgical tool inserted into the abdominal cavity laparoscopically. With the uterine manipulator device in place, the surgeon uses a laparoscopic surgical tool to grasp the notches of the first and second wires and pivot the wires about the connection points on the rim of the cervical cup, cauterizing tissue in the process.

The uterine manipulator device may also include an occluding cup that is movable along the shaft and positioned against the cervical cup during use to block the escape of gas and smoke from the abdominal cavity through the vaginal canal. Lumens or cannulas extending through the cervical and occluding cups cycle gas into and out of the abdominal cavity to remove the smoke from the abdominal cavity and maintain a clear view the operative field.

An objective of the present design is to minimize the number of tools necessary for a hysterectomy or related procedure by incorporating the cutting or cauterization tool into the uterine manipulator device.

An advantage of the present design is to minimize potential errors in cauterization by providing a stable surface in the cervical cup against which the heated element, cauterization wire, or cutting tool is secured.

A further advantage of the present application is the improved identification of the specific area to be cut or cauterized as well as the pelvic anatomy to be protected and avoided during a surgical procedure through the use of transillumination.

Another advantage of the present design is to provide adequate air flow through the abdominal cavity with sufficiently sized lumens or cannulas.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitation. In the figures, like reference numerals refer to the same or similar elements.

FIG. 2 is a front elevational view of the uterine manipulator device of FIG. 1.

FIG. 3 is a side elevational view of the uterine manipulator device of FIG. 1 without the lumens.

FIGS. 5A-5C are plan views of the uterine manipulator device of FIG. 1 without the light source in a fully open position, a partially open position, and a fully closed position, respectively.

FIGS. 6A-6C are front elevational views of the uterine manipulator device the fully open position, the partially open position, and the fully closed position of FIGS. 3A-3C, respectively.

DETAILED DESCRIPTION OF THE INVENTION

Figure 1:
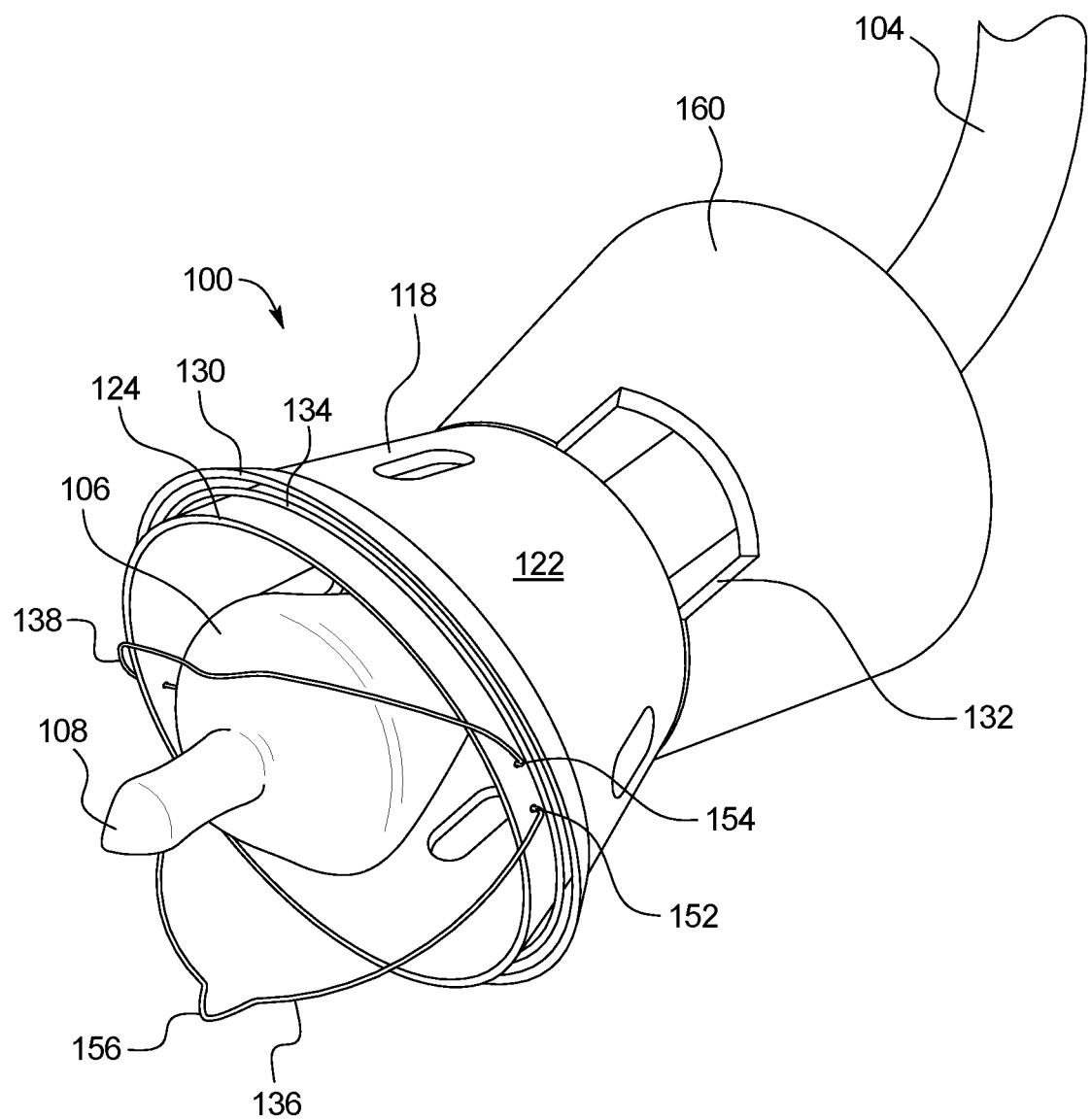
FIG. 1 is a perspective view of a uterine manipulator device of the present application.

FIGS. 1-4 illustrate a uterine manipulator device 100 that is inserted through a patient's vaginal canal 102 during female pelvic surgery. The uterine manipulator device 100 includes a rigid shaft 104 with a balloon 106 positioned at a distal end 108. A handle 110 may be attached to a proximal end 112 of the shaft 104. During a procedure, the deflated balloon 106 is inserted into the patient's uterus 114 and then filled with water or other fluid. Separately, a camera inserted laparoscopically into the abdominal cavity 116 provides a view of the operative field, and the surgeon can move the uterus 114 by manipulating the handle 110 of the shaft 104 in order to view anatomy around the uterus 114 through the camera imaging.

Figure 4A:
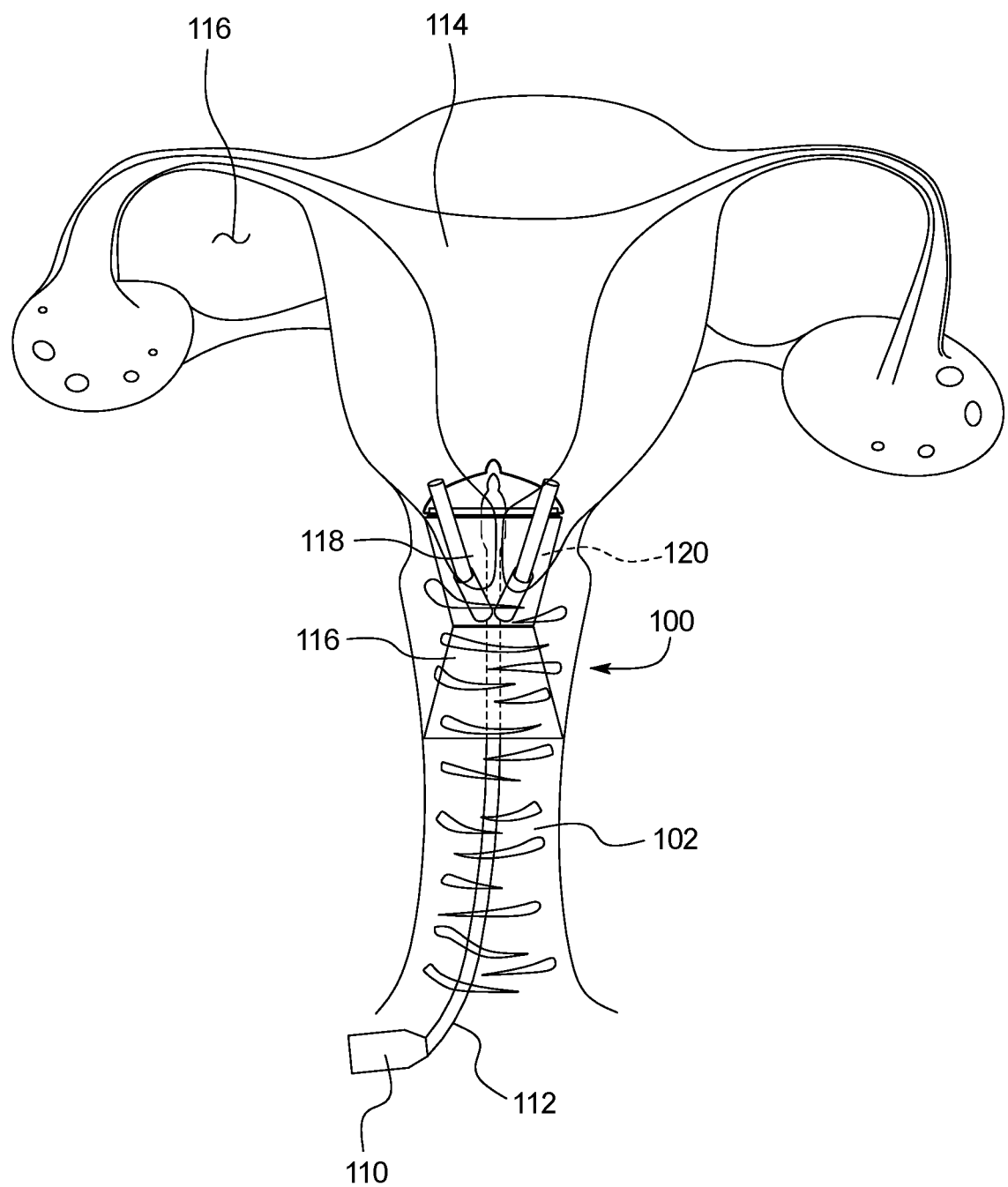
FIG. 4A is a schematic of the uterine manipulator device of FIG. 1 positioned on the cervix of a patient.

Referring to FIG. 4A, a cervical cup 118 is positioned on the shaft 104 adjacent the distal end 108 and receives the cervix 120 during use. Seen best in FIGS. 2 and 3, an annular wall 122 having a frustoconical shape with a rim 124 extends from a base 126. The shaft 104 protrudes through an opening 128 within the base 126 as shown in FIGS. 5A-5C so that the distal end 108 is adjacent to the rim 124 of the cervical cup 118. In some embodiments, the cervical cup 118 is movable along and releasably secured to the shaft 104, while in other embodiments the cervical cup 118 is permanently affixed to the shaft 104. In the illustrated embodiment, the cervical cup 118 includes a ledge 130 outwardly protruding from the annular wall 122 slightly spaced from the rim 124.

In the process of positioning the uterine manipulator device 100 on the cervix 120, the surgeon may use a clamp (not shown) or other fastening device to hold the cervix 120 in place. The cervical cup 118 of the present application includes a clamp opening 132 through which the clamping tool may positioned.

The cervical cup 118 may further include a light source 134 to illuminate the surgeon's operative field. In the illustrated example, a light source 134 such as a fiber optic or a plurality of light emitting diodes is provided around the rim 130 of the cervical cup 118 around the cervical cup 118 and rim 130 of the cervical cup 118. During a surgical procedure, the operative field is viewed through a camera within the abdominal cavity. The light source 134 on the cervical cup 118 transilluminates the cervix 120 so that the surgeon can determine where the cervical cup 118 is located in the camera imaging. The transillumination also allows the surgeon to identify pelvic anatomy such as the uterine arteries and the ureter. The light source 134 may be powered from an external source, or may be powered by a battery or other power source within the handle 110 of the uterine manipulator device 100. The surgeon may activate the light source using a switch on the handle 100. The light source 134 may be used with any embodiment described herein.

Figure 4B:
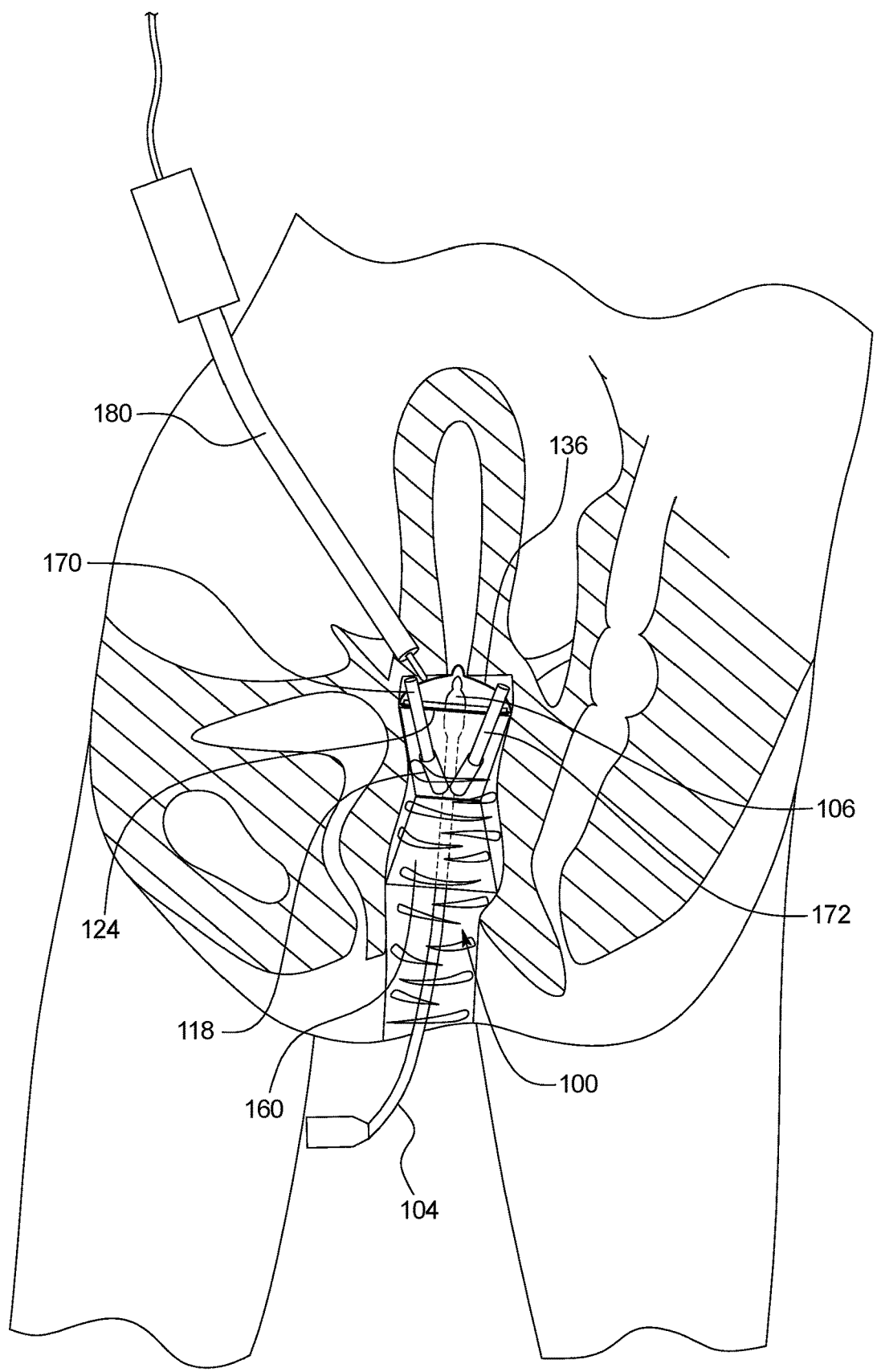
FIG. 4B is a schematic of the uterine manipulator device of FIG. 1 positioned on the cervix of a patient.

Referring to FIGS. 5A-5C and 6A-6C, first and second cauterizing wires 136, 138 are rotatably connected to the rim 130 of the cervical cup 118. Specifically, each wire 136, 138 has a hemispherical shape with a first end 140, 142 and a second end 144, 146 extending through the rim 130 of the cervical cup 118 at a first connection point 148, 150 and a second connection point 152, 154, respectively, opposite of one another. Each wire 136, 138 may include a notch 156, 158 centrally located between the first and second ends 140-146 to be grasped by a surgical tool during a procedure. The ends 140-146 of the first and second wires 136, 138 are positioned next to one another so that the wires 136, 138 extend along the perimeter of the rim 130 in an inactive position shown in FIGS. 4A and 5A. Partial rotation of the first and second wires 136, 138 is shown in FIGS. 4B and 5B. Positioning of the first and second wires 136, 138 in the fully closed position is illustrated in FIGS. 4B and 5C. In the illustrated embodiment, each of the first and second wires 136, 138 pivots approximately 90 degrees about the respective connection points 148-154 to provide a full 180-degree rotation. In other embodiments, the uterine manipulator device 100 may include a single wire that pivots approximately 180 degrees about opposing connection points or any number of wires as desired. Still further, other embodiments may include an alternative heating element or other cutting tool in lieu of the first and second cauterizing wires.

Once the uterine manipulator device 100 has been positioned and the patient's cervix 120 is in the cervical cup 118, the wires 136, 138 are energized to cauterize tissue at the cervical/vaginal junction, thereby detaching the uterus from the vagina. The first and second wires 136, 138 are energized by a current from a power source. In one embodiment, a power source such as a battery is mounted within the handle 110 of the uterine manipulator device 100. The surgeon may activate the wires 136, 138 using a switch on the handle 100. In another embodiment shown in FIG. 4B, the wires 136, 138 may be energized by a power source on a surgical tool 180 inserted into the abdominal cavity laparoscopically. With the uterine manipulator device 100 in place, the surgeon inserts a surgical tool laparoscopically to elevate and pivot the wires 136, 138 about the connection points 148-154 on the rim 130 of the cervical cup 118, cauterizing tissue in the process.

To contain the smoke produced by the cauterization within the abdominal cavity 116, an occluding cup 160 movable along the shaft 104 as shown in FIGS. 1-3 is positioned against the cervical cup 118 during use as shown in FIG. 4A. Similar to the cervical cup 118, the occluding cup 160 in the illustrated embodiment includes an annular wall 162 having a frustoconical shape extending from a base 164 with an opening 166 through which the shaft 104 protrudes. Also like the cervical cup 118, the occluding cup 160 may include a clamp opening 168 as well. Still further, in other embodiments, the occluding cup 160 may comprise an expandable balloon cuff such as the vaginal occluder described in U.S. Pat. No. 8,545,513.

The uterine manipulator device 100 may include lumens 170, 172 to cycle gas into and out of the abdominal cavity 116 to remove smoke while distending the abdominal cavity 116 to provide a clear view the operative field. With the uterine manipulator device 100 in place, gas is injected into the abdominal cavity 116 through a first lumen 170 and exits the abdominal cavity 116 through a second lumen 172. The first and second lumens 170, 172 extend through lumen openings of the rim 130 of the cervical cup 118. During use, a source of gas is attached to the first lumen 170 and a vacuum is attached to the second lumen 172 near the proximal end 112 of the uterine manipulator device 110.

Figure 7:
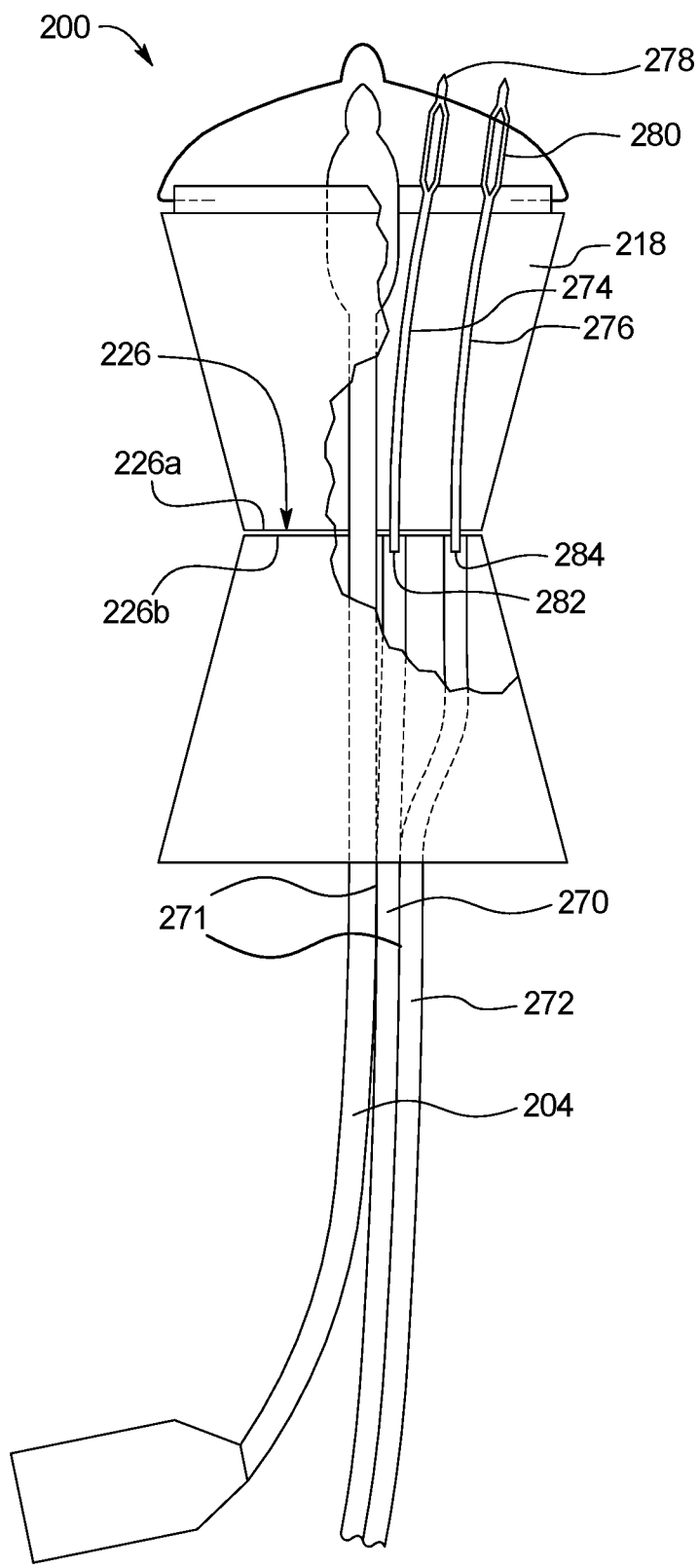
FIG. 7 is a front elevational view of an alternative uterine manipulator device of the present application, with a broken view of first and second lumen ports.

In an alternative uterine manipulator device 200 shown in FIG. 7, the first and second lumens 270, 272 cycle gas through the abdominal cavity 116 through first and second ports 274, 276, respectively, through the base 226 of the cervical cup 218. The first and second ports 274, 276 project from an interior surface 226a of the base 226. Fenestrations 278, 280 on the first and second ports 274, 276, respectively, prevent potential suction injury of intraabdominal contents. On the end opposite of the first and second fenestrations 274, 276, respectively, the first and second ports 274, 274 include first and second coupling features 282, 284, respectively, which extend through the lumen openings on the occluding cup 260. The first and second lumens 270, 272 are secured to the first and second coupling features, 282, 284, respectively, of the cervical cup prior to insertion. In the embodiment illustrated in FIG. 7, the first and second lumens 270, 272 are secured together and to the shaft 204 at a connection point 271. The uterine manipulator device 200 may also include a light source around the rim of the cervical cup 218.

Figure 8:
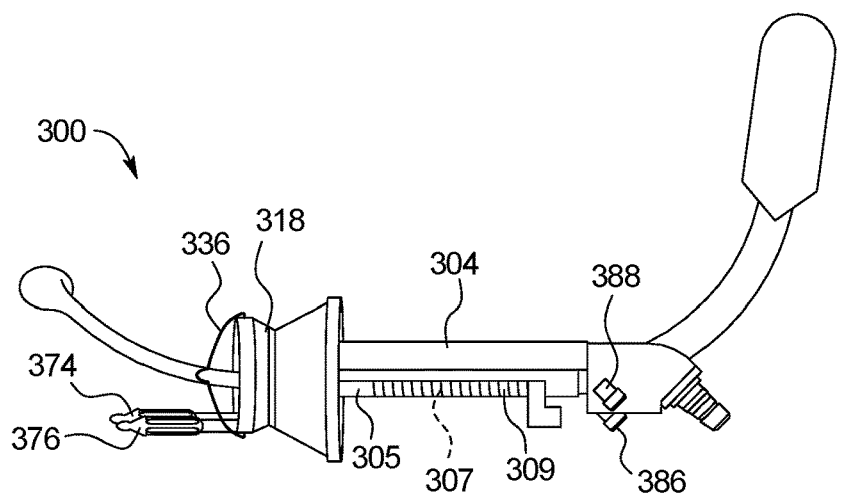
FIG. 8 is a side elevational view of an alternative uterine manipulator devices of the present application including a multi-lumen shaft housing.

In an alternative uterine manipulator device 300 illustrated in FIG. 8, a cervical cup 318 is mounted to the multi-lumen shaft housing 304 that includes a bracket 305 for receiving the clamping tool (not shown). A clamp for securing the device 300 to the cervix 120 extends from the cervical cup 318 away from the multi-lumen shaft housing 304. The clamp is secured to a bracket 305 on the multi-lumen shaft housing 304 and retracted inwardly by a spring 307 housed within a slotted cover 309 along the length of the multi-lumen shaft housing 304. Similar to the embodiment illustrated in FIG. 7, first and second ports 374, 376 extend from the base of the cervical cup 318. The first and second lumens are positioned within the multi-lumen shaft housing 304, which includes first and second connection hubs 386, 388 that are connected to a gas source and a vacuum, respectively, during use. The uterine manipulator device 300 may also include a light source around the rim of the cervical cup 318.

Figure 9:
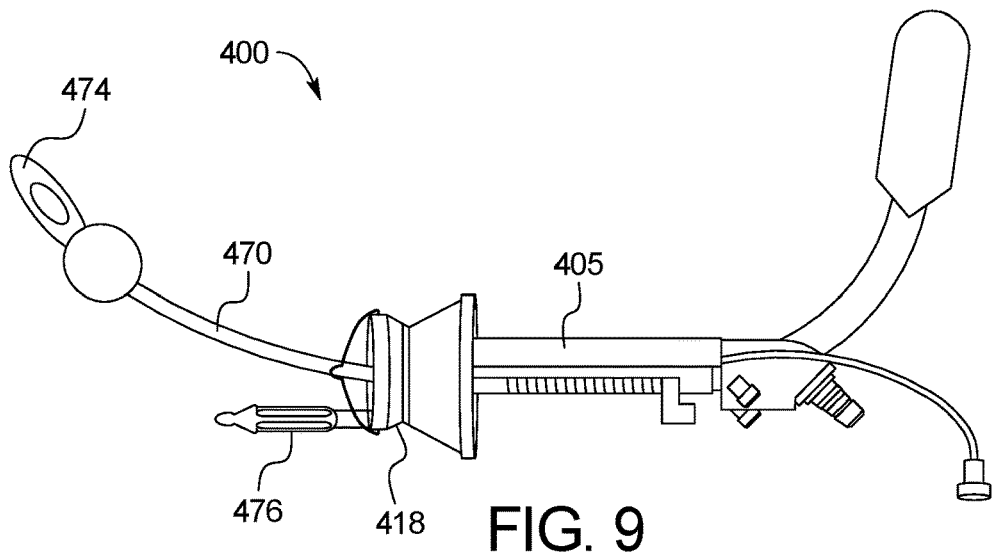
FIGS. 9 and 10 are side elevational views of alternative uterine manipulator device of the present application illustrating intrauterine mechanisms.

FIG. 9 illustrates a further embodiment uterine manipulator device 400 including a first lumen port 474 extending from a uterine sound or lumen 470 that is inserted through the rigid multi-lumen shaft housing 405. A second lumen port 476 extends from the base of the cervical cup 418. Additional lumens may be incorporated into the uterine manipulator device 400 to irrigate the uterus and/or abdominal cavity or to inject additional fluids.

Figure 10:
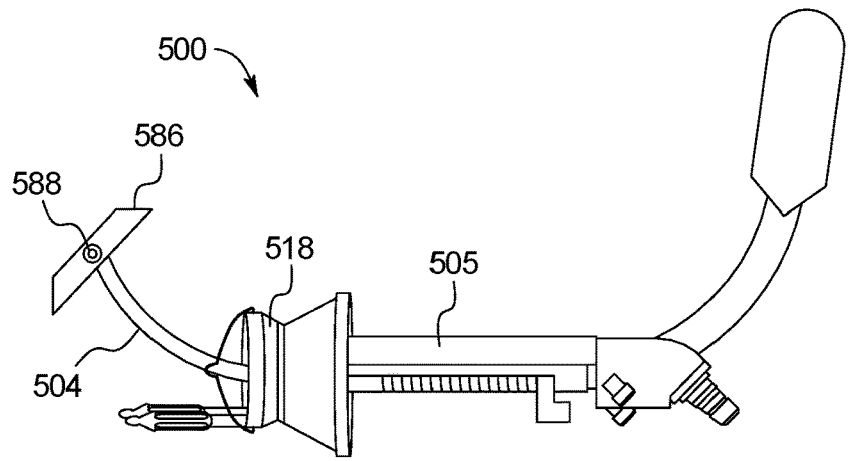

In a further embodiment uterine manipulator device 500 illustrated in FIG. 10, an anchoring mechanism 586 extends from a uterine sound or probe 504 that hinges about a pivot point 588. The length of the anchoring mechanism 586 is positioned parallel to the sound 504 during insertion, and may be rotated about the pivot point 588 once inside of the uterus 114.

It should be noted that various changes and modifications to the presently preferred embodiments described herein will be apparent to those skilled in the art. Such changes and modifications may be made without departing from the spirit and scope of the present invention and without diminishing its attendant advantages.

I claim:

1. A method of cauterizing tissue of a patient, comprising: providing a uterine manipulator device comprising:
    a shaft including a proximal end and a distal end;
    a cervical cup positioned on the shaft near the distal end, wherein the cervical cup includes a first base and a first annular wall with a rim, and wherein the first base includes a first opening to receive the shaft; and
    a heated element along the rim of the cervical cup that is rotatably coupled to the rim, wherein the heated element comprises a wire for cauterizing tissue, wherein the wire includes a first end and a second end, each of the first and second ends being rotatably connected to the rim of the cervical cup at first and second connection points, respectively; and
  inserting the uterine manipulator device into a vaginal cavity of a patient so that a cervix of the patient is received by the cervical cup of the uterine manipulator device;
  energizing the heated element and rotating the heated element about the first and second connection points to cauterize tissue of the patient.

2. The method of claim 1, wherein the heated element comprises the wire and a further wire, wherein the further wire includes a further first end and a further second end, each of the further first and second ends being rotatably connected to the rim of the cervical cup at further first and second connection points, respectively.

3. The method of claim 2, wherein the uterine manipulator device further comprises a light source adjacent to the rim of the cervical cup.

4. The method of claim 3, wherein the uterine manipulator device further comprises first and second lumens extending through the cervical cup.

5. The method of claim 1, further comprising the step of providing an energy source through the device to energize the heated element.

6. The method of claim 1, further comprising the step of inserting a surgical tool laparoscopically through the patient's abdomen to access the uterine manipulator device and energize the heated element.

7. The method of claim 1, further comprising the step of laparoscopically accessing the device through the patient's abdomen to pivot the heated element about the rim of the cervical cup.

* * * * *